United States Patent [19]

Michaely et al.

[11] Patent Number: 5,073,642

[45] Date of Patent: Dec. 17, 1991

[54] TRISUBSTITUTED BENZOIC ACID INTERMEDIATES

[75] Inventors: William J. Michaely, El Cerrito; Jeff K. Curtis, Berkeley, both of Calif.

[73] Assignee: ICI Americas Inc., Wilmington, Del.

[21] Appl. No.: 624,933

[22] Filed: Dec. 10, 1990

Related U.S. Application Data

[62] Division of Ser. No. 386,648, Jul. 31, 1989, Pat. No. 5,001,256, which is a division of Ser. No. 273,391, Nov. 18, 1988, abandoned.

[51] Int. Cl.$^5$ .................... C07C 323/20; C07C 255/50
[52] U.S. Cl. ...................................... 560/18; 558/411; 558/412; 562/432
[58] Field of Search ................... 558/411, 412; 560/18; 562/432

[56] References Cited

U.S. PATENT DOCUMENTS

| 3,013,055 | 12/1961 | Richter | 562/474 |
| 3,334,125 | 8/1967 | Richter | 560/62 |

FOREIGN PATENT DOCUMENTS

| 0108526 | 5/1984 | European Pat. Off. |
| 0195247 | 9/1986 | European Pat. Off. |
| 42-7451 | 3/1967 | Japan |

OTHER PUBLICATIONS

Tetrahedron, vol. 44, No. 6, (1988), pp. 1631-1636.

*Primary Examiner*—Jose G. Dees
*Assistant Examiner*—Vera C. Clarke
*Attorney, Agent, or Firm*—Edwin H. Baker

[57] ABSTRACT

Novel trisubstituted benzoic acid intermediates which are useful in the preparation of certain herbicidal 2-(2,3,4-trisubstituted benzoyl)-1,3-cyclohexanediones are described.

2 Claims, No Drawings

TRISUBSTITUTED BENZOIC ACID INTERMEDIATES

This is a divisional of application Ser. No. 07/386,648 filed July 31, 1989, now U.S. Pat. No. 5,001,256 which is a divisional of application Ser. No. 07/273,391, filed Nov. 18, 1988, now abandoned.

BACKGROUND OF THE INVENTION

Certain 2-(2'2'4'tri-substituted benzoyl)-1,3-cyclohexanedione herbicides are described in U.S. Pat. No. 4,780,127, issued Oct. 25, 1988, U.S. application Ser. No. 129,026, filed Dec U.S. application entitled 2-(2',3',4'-trisubstituted benzoyl)-1,3-cyclo-hexanediones, with William J. Michaely, inventor, filed herewith, and all incorporated herein by reference.

The above-described herbicidal compounds can have the following structural formula

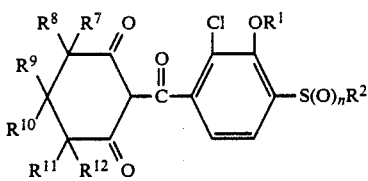

wherein $R^7$ through $R^{12}$ are hydrogen or $C_1-C_4$ alky $C_1-C_4$ haloalkyl, $CH_2CH_2-OCH_3$, $CH_2CH_2OC_2H_5$, $CH_2CH_2SCH_3$, or $CH_2CH_2SC_2H_5$; $R^2$ is $C_1-C_4$ alkyl; and n is the integer 0 or 2.

These herbicides can be prepared ty reacting a dione of the structural formula

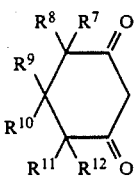

wherein $R^7$ through $R^{12}$ are as defined with a mole of trisubstituted benzoyl chloride of the structural formula

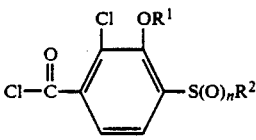

wherein n, $R^1$ and $R^2$ are as defined above.

DESCRIPTION OF THE INVENTION

This invention has several embodiments which are as follows:

Embodiment A relates to novel intermediate compounds having the structural formula

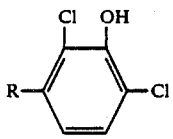

wherein R is cyano; carboxy; or $-CO_2R_a$ where $R_a$ is $C_1-C_4$, alkyl, preferably ethyl; most preferably R is $-CO_2C_2H_5$.

Embodiment B relates to novel intermediate compounds having the structural formula

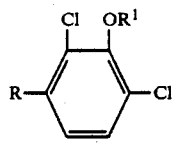

wherein R is cyano; carboxy or $-CO_2R_a$ wherein $R_a$ is $C_1-C_4$ alkyl, preferably ethyl, most preferably R is $-CO_2C_2H_5$ and $R^1$ is $C_1-C_4$ alkyl; preferably $C_1-C_2$ alkyl; $C_1-C_4$ haloalkyl; $-CH_2CH_2OCH_3$; $-CH_2CH_2OC_2H_5$; $-CH_2CH_2SCH_3$ or $-CH_2CH_2SC_2H_5$, with the proviso that when R is carboxy, then $R^1$ is $-CH_2CH_2OCH_3$; $-CH_2CH_2OC_2H_5$; $-CH_2CH_2SCH_3$ or $-CH_2CH_2SC_2H_5$.

Embodiment C relates to novel intermediate compounds having the structural formula

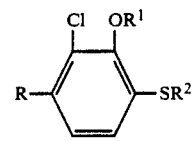

wherein R is cyano; carboxy or $-CO_2R_a$ wherein $R_a$ is $C_1-C_4$ alkyl, preferably ethyl, most preferably R is $CO_2C_{2l}H_5$; $R^1$ is $C_1-C_4$ alkyl; $C_1-C_4$ haloalkyl; $-CH_2CH_2OCH_3$, $-CH_2CH_2OC_2H_5$, $-CH_2CH_2SCH_3$ or $-CH_2CH_2CH_2SC_2H_5$ and $R^2$ is $C_1-C_4$- alkyl, preferably methyl, ethyl or n-propyl with the proviso that when R is carboxy, then $R^1$ is $-CH_2CH_2OCH_3$; $CH_2CH_2OC_2H_5$, $-CH_2CH_2SCH_3$ or $-CH_2CH_2SC_2H_5$.

Embodiment D relates to novel intermediate compounds having the structural formula

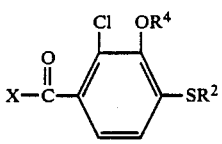

wherein X is chlorine or hydroxy; $R^4$ is $-CH_2CH_2OCH_3$, $-CH_2CH_2OC_2H_5$, $-CH_2CH_2SCH_3$ or $CH_2CH_2SC_2H_5$, preferably $-CH_2CH_2OCH_3$ or $-CH_2CH_2OC_2R^2$ is $C_1-C_4$ alkyl, preferably methyl, ethyl or propyl.

Embodiment E relates to novel intermediate compounds having the structural formula

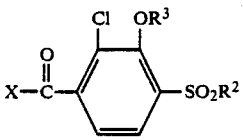

wherein X is hydroxy or chlorine; $R^3$ is $-CH_2CH_2OCH_3$ or $-CH_2CH_2OC_2H_5$ and $R^2$ is $C_1-C_4$ alkyl, preferably methyl, ethyl or n-propyl.

Embodiment F relates to novel intermediate compounds having the structural formula

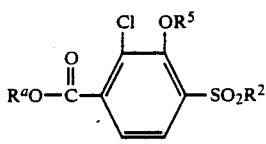

wherein $R^a$ is $C_1-C_4$ alkyl, preferably ethyl, $R^5$ is $C_1-C_4$ alkyl; $C_1-C_4$ haloalkyl; $-CH_2CH_2OCH_3$ or $-CH_2CH_2OC_2H_5$; preferably $-CH_2CH_2OCH_3$ or $-CH_2CH_2OC_2H_5$ and $R^2$ is $C_1-C_4$ alkyl, preferably methyl, ethyl or n-propyl.

In embodiments A-C, the group R can also be trifluoromethyl.

The several intermediate compounds of this invention can be prepared by the general method shown in the Figure of the next page with R, $R^1$, $R^2$ and $R^5$ being as defined. The group $R^z$ is $C_1-C_4$ alkyl.

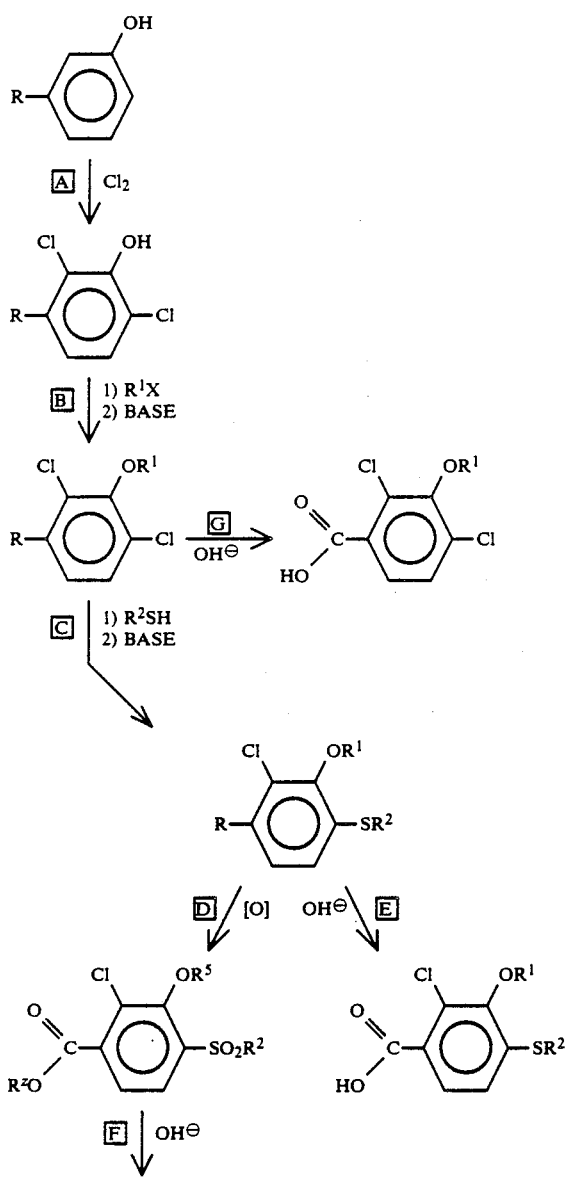

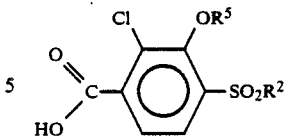

Referring to the Figure, and particularly to Reaction Steps (A) through (G), consider the following:

Generally in Reaction Step (A), a mole amount of the 3-substituted phenol is reacted with 2 moles of chlorine and a cat a $C_1-C_{10}$ alkylamine, preferably tert-butylamine or diisopropylamine in a solvent such as methylene chloride, at a temperature between $-70°$ C. to $70°$ C. After this reaction, the free chlorinated phenol is isolated by normal procedures.

For Reaction Step (B), one mole of the dichloro-substituted phenol reaction product of Step (A) is reacted with an appropriate alkylating agent such as a 2-chloroethyl ethyl ether, 2-chloroet ether, 2-chloroethyl xethyl sulfide, 2-chloroethyl ethyl sulfide or $C_1-C_4$ alkylchloride along with a catalytic amount of potassium iodide and a mole excess of a base such as potassium carbonate. Alkyl iodides such as methyl iodide or ethyl iodide may also be used. In these cases the catalytic potassium iodide is not needed and little or no heat is required. The reaction is run at $25°$ C. to $80°$ C. for 4 hours with agitation. The reaction product is recovered by conventional techniques.

For Reaction Step (C), the dichloro compound from Reaction Step (B) is reacted with an equal mole amount of a $C_1-C_4$ alkyl mercaptan along with a mole excess of a base such as potassium carbonate in a solvent such as dimethylforamide. The reaction is run for several hours at a temperature between $50°$ C. to $100°$ C. with stirring under nitrogen. The desired reaction product is recovered by conventional techniques.

For Reaction Step (D) a mole amount of the alkyl ester of 2-chloro-4-alkylthio benzo compound is oxidized with at least 3 moles of an oxidizing agent such as chloroperbenzoic acid in a suitable solvent such as xethylene chloride by stirring a solution of the reactant at $20°$ to $100°$ C. The desired intermediate is recovered by conventional techniques. During this reaction step the 4-alkylthio substitute to the corresponding alkylsulfone.

For Reaction Step (E) a mole amount of the 2-chloro-3-substituted-4-alkylthio ester or cyano compound is hydro as sodium hydroxide to the corresponding 2-chloro-3-substituted-4-alkylthio benzoic acid. The hydrolysis is run in a solvent cent methanol-water mixture. The reaction can be run at $25°-100°$ C. with stirring. The desired product is recovered by conventional techniques.

For Reaction Step (F) the alkyl ester of the trisubstituted benzoic acid is converted to the trisubstituted benzoic acid by the hydrolysis step taught in Reaction Step (E)

In the alternative, the tri-substituted benzoic acid reaction product of Reaction Step (F) can be directly prepared from the reaction product of Reaction Step (C) by a combination hydrolysis of the 2-chloro3-substituted-4-alkylthio ester or cyano compound to benzoic acid and an oxidation of the 4-alkylthio substituent to the corresponding 4-alkylsulfone. The hydrolysis and oxidation steps can be jointly carried out by reacting a mole of the ester or cyano compound with at least 5 moles of sodium or calcium hypochlorite in a suitable solvent such as dioxane-water, by heating a solution of the reactants from about 25° C. to about 100° C., followed by the acidification with concentrated hydrochloric acid. Filtration of the resulting precipitate yields the desired product.

For Reaction Step (G) the dichloro compound from Reaction Step (B) is converted to the benzoic acid by the hydrolysis step taught in Reaction Step (E).

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as xethylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The trisubstituted benzoic acid chloride intermediates are useful in the preparation of the previously described herbicidal 2',3',4'-trisubstituted benoyl-1,3-cyclohexazediones.

The following series of examples teach the synthesis of representative intermediate compounds of this invention. The structures of all compounds of the examples and table were verified by nuclear magnetic resonance (NMR), infrared spectroscopy (IR) and mass spectroscopy (MS).

EXAMPLE 1

Ethyl 2,4-chloro-.3-hydroxybenzoate

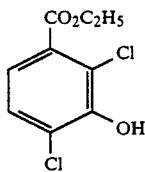

In a 3-neck, 1-liter flask equipped with a xechanical stirrer, condenser, thermometer and a diffusion tube was added a solution of 106 grams (0.64 mole) ethyl 3-hydroxybenzote and 0.5 grams diisopropylamine in 600 milliliters (ml) dichloroethane at reflux. Chlorine (112 grams, 1.6 mole) was added through the diffusion tube over a period of 6 hours then let cool to room temperature. After cooling, the solution was washed with 200 ml 5% sodium bisulfite solution, then with 200 ml water, dried (MgSO$_4$) and reduced under vacuum. Yield was 151 g of an oil. This mixture·of chlorinated compounds (66% above product) can b ether/pentane by cooling to −20° C. to give pure ethyl 2,4-dichloro-3-hydroxybenzoate. The structure of this compound and all examples were verified by nuclear magnetic resonance (NMR), infrared spectroscopy (IR) and xass spectroscopy (MS).

Additional compounds were prepared by the same procedure as described in Example 1 and are listed in Table 1.

TABLE 1

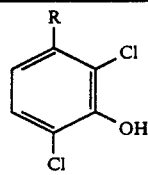

| R | Yield (%) | m.p. °C. |
|---|---|---|
| CO$_2$CH$_3$ | 72 | 57–64 |
| CO$_2$CH(CH$_3$)$_2$ | 66 | oil |

EXAMPLE 2

Ethyl 2,4-chloro-3-(2-methoxyethyoxy) benzoate

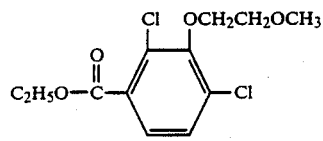

A solution of 18 g (77 millimoles, xmol) ethyl 2,4-dichloro-3hydroxybenzorte, 22 g (3 equivalents) (eq) g (2 eq) potassium carbonaate and ca. 0.5 9 sodium iodide in 100 ml DMF was heated at 80° C. for 1.5 hours. To the cooled solution was added 400 xl ether. The organic phase was washed with 100 xl water (2 times), 100 xl OH and 100 ml 10% HCl. Dried (MgSO$_4$) and reduced under vacuum. The yield was 20 g (68 mole).

Additional compounds were prepared by the same procedure as described in Example 2 (except in those cases using alkyl iodide then the potassium iodide catalyst was omitted and little or no heat is required) and are listed in Table 2

TABLE 2

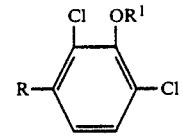

| R | R$^1$ | Physical Property | Yield (%) |
|---|---|---|---|
| CO$_2$C$_2$H$_5$ | C$_2$H$_5$ | oil | 92 |
| CO$_2$C$_2$H$_5$ | n-C$_3$H$_7$ | oil | 100 |
| CO$_2$C$_2$H$_5$ | CH$_2$CH$_2$OCH$_3$ | oil | 30 |
| CO$_2$C$_2$H$_5$ | CH$_2$CH$_2$Br | oil | 95 |
| CO$_2$C$_2$H$_5$ | CH$_2$CH$_2$SCH$_2$H$_5$ | oil | 66 |
| CO$_2$C$_2$H$_5$ | CH$_2$CH$_2$Cl | oil | 10 |
| CO$_2$CH$_3$ | CH$_2$CF$_3$ | solid | 57 |

EXAMPLE 3

Ethyl 2-chloro-3-(2-methoxyethoxy)-4-ethylthi9obenzoate

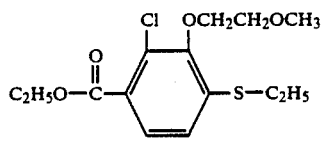

A solution of 10 g (34 mmole) ethyl 2,4-dichloro-3-(2-methoxyethoxy)benozate, 10 g (4 eg) ethanethiol and 10 g (2 eg) potassium carbonate in 100 ml DMF was heated (approximately 100° C.) for 2 hours, then let cool overneigh. Added 400 ml diethyl ether and washed with 100 ml water (two times), 100 ml 10% HCl and 100 ml 10% NaOH. Dried (MgSO4) and reduced under vacuum. Yield 10 g (31 mmole) of an oil.

Additional compounds were prepared by the same procedure as described in Example 3 and are listed in Table 3.

TABLE 3

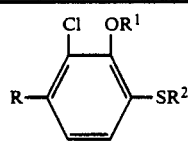

| R | R¹ | R² | Yield (%) |
|---|---|---|---|
| CO$_2$C$_2$H$_5$ | C$_2$H$_5$ | C$_2$H$_5$ | 64 |
| CO$_2$C$_2$H$_5$ | n-C$_3$H$_7$ | CH$_3$ | 41 |
| CO$_2$C$_2$H$_5$ | CH$_2$CH$_2$OCH$_3$ | C$_2$H$_5$ | 46 |
| CO$_2$C$_2$H$_5$ | CH$_2$CH$_2$OCH$_3$ | n-C$_3$H$_7$ | 86 |
| CO$_2$C$_2$H$_5$ | H | C$_2$H$_5$ | 15 |
| CO$_2$CH$_3$ | H | C$_2$H$_5$ | — |
| CO$_2$CH$_3$ | CH$_2$CH$_2$OCH$_3$ | C$_2$H$_5$ | 90 |
| CO$_2$CH$_3$ | CH$_2$CH$_2$OCH$_3$ | n-C$_3$H$_7$ | 87 |
| CO$_2$CH$_3$ | CH$_2$CH$_2$OCH$_3$ | CH$_3$ | 65 |
| CO$_2$CH$_3$ | CH$_2$CF$_3$ | C$_2$H$_5$ | 53 |

EXAMPLE 4

Ethyl 2-chloro-3-(2-methoxyethoxy)-4-ethylsulfonyl benzoate

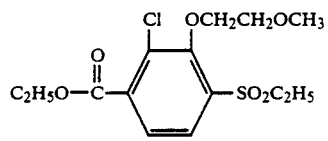

The ester, ethyl 2-chloro-3-(2-methoxyethoxy)-34-ethylthiobenzoate from Example 3 (10 g) was dissolved in 100 ml of methylene chloride and cooled with an ice bath. Next 18 g solid m-chloroperoxybenzoic acid (85% pure, 2.2 equivalents) was added in portions over a period of 2 hours. The crude reaction mixture was allowed to warm to room temperature. After 1 hour at room temperature the excess peracid was destroyed with sodium bisulfite (100 ml 5% solution). The organic layer was washed two times with 5% sodium hydroxide (100%) and stripped under vacuum to give 11.3 grams of pure ethyl 2-chloro-3-(2-methoxyethoxy)-4-ethylsulfonylbenzoate as a viscous oil.

Additional compounds were prepared by the same procedure as described in Example 4 and are listed in Table 4.

TABLE 4

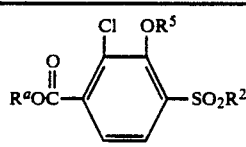

| R$^a$ | R⁵ | R² | Yield (%) |
|---|---|---|---|
| C$_2$H$_5$ | C$_2$H$_5$ | C$_2$H$_5$ | 90 |
| C$_2$H$_5$ | n-C$_3$H$_7$ | CH$_3$ | 64 |
| C$_2$H$_5$ | C$_2$H$_4$OCH$_3$ | C$_2$H$_5$ | 72 |
| C$_2$H$_5$ | C$_2$H$_4$OCH$_3$ | n-C$_3$H$_7$ | 98 |
| CH$_3$ | CH$_2$CH$_2$Cl | n-C$_3$H$_7$ | — |
| CH$_3$ | C$_2$H$_4$OCH$_3$ | C$_2$H$_5$ | 100 |

TABLE 4-continued

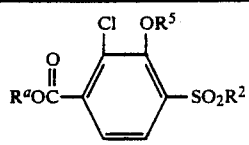

| R$^a$ | R⁵ | R² | Yield (%) |
|---|---|---|---|
| CH$_3$ | C$_2$H$_4$OCH$_3$ | n-C$_3$H$_7$ | 97 |
| CH$_3$ | CH$_2$CH$_2$OCH$_3$ | CH$_3$ | 87 |
| CH$_3$ | CH$_2$CF$_3$ | CH$_3$ | — |

EXAMPLE 5

2-chloro-3-(2-methoxyethoxy)-4-ethylsulfonylbenzoic acid

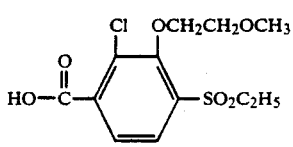

To 11.3 g (0.03 mole) of the ethyl 2-chloro-3-(2-methoxyethoxy)-4-ethylfsulfonylbenzoate in 100 ml of 96% ethanol was added dropwise 16 ml 1.2 eq) of 10% sodium hydroxide. After stirring at room temperature for 4 hours, 100 ml of diethyl ether was added and the organic phase was extracted with 50 ml of 5% NaOH. The aqueous phase was acidified with 10% HCl and extracted two times with 50 ml chloroform. The organic phase was dried with MgSO4 and concentrated under vacuum to yield 8.8 grams of 2-chloro-3-(2-methoxyethoxy)4-ethylsulfonylbenzoic acid as a viscous oil.

Additional compounds were prepared by the same procedure as described in Example 5 and are listed in Table 5.

TABLE 5

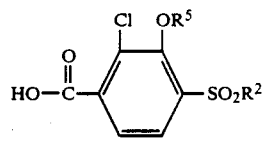

| R⁵ | R² | Yield (%) |
|---|---|---|
| CH$_2$CH$_2$OCH$_3$ | n-C$_3$H$_7$ | 77 |
| CH$_2$CH$_2$OCH$_3$ | CH$_3$ | 80 |

EXAMPLE 6

2-Chloro-3-(2-methoxyethoxy)-4-ethylthio benzoic acid

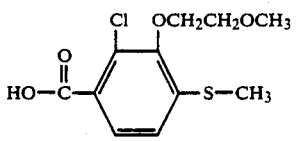

Three grams (8.2 mmol ethyl 2chloro-3-(2-methoxethoxy)-4-propanethiobenzoate was dissolved in 20 ml 96% ethyl alcohol. To this was added 3.9 ml 10% sodium hdyroxide in water. After stirring 4 hours at room temperature, 100 ml of diethyl ether was added to the solution. The solution was extracted twice with 50 ml 5% sodium hydroxide solution. The combined caustic extracts were acidified with 10% hydrochloric acid and extracted twice with 50 ml portions of chloroform. The chloroform extracts were dried over magnesium sulfate and the chloroform removed in vacuo to afford the free acid (2.0 g, 72%) as a softy solid.

Additional compounds were prepared by the same procedure as described in Example 6 and are listed in Table 6.

TABLE 6

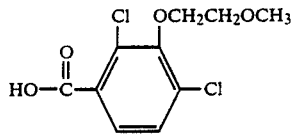

| $R^1$ | $R^2$ | Yield (%) |
|---|---|---|
| $CH_2CH_2OCH_3$ | $C_2H_5$ | 72 |

EXAMPLE 7

2,4-Dichloro-3-(2-methoxyethoxy) benzoic acid

Sixteen grams (41 mmol) ethyl 2,4-dichloro-3-(2-methoxyethoxy)benzoate was dissolved in 100 ml of 96% ethanol. To this was added, in portions, 18 ml (ca 1.1 equivalents) 10% sod hours at room temperature, 250 ml diethyl ether was added to the solution. The solution was extracted twice with 50 ml 5% sod combined caustic extracts were acidified with a 10% hydrochloric acid solution and extracted twice with 75 ml portions of chloroform. The chloroform extracts were dried (magnesium sulfate) and the chloroform removed in vacuo to afford the free acid (12.8 g, 79%) as a white solid.

Additional compounds were prepared by the same procedure as described in Example 7 and are listed in Table 7.

TABLE 7

| $R^1$ | Yield (%) |
|---|---|
| $CH_2CH_2SC_2H_5$ | 100 |

The above-described benzoic acids can be readily converted to their acid chlorides using oxalyl chloride and a catalytic amount of ethylformamide. These acid chlorides can be reacted with the above-described 1,3-cyclohexanedione to prepare the above-described herbicid 2,3,4-trisubstituted benzoyl-1,3-cyclohexanediones according to the following two-step reaction:

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

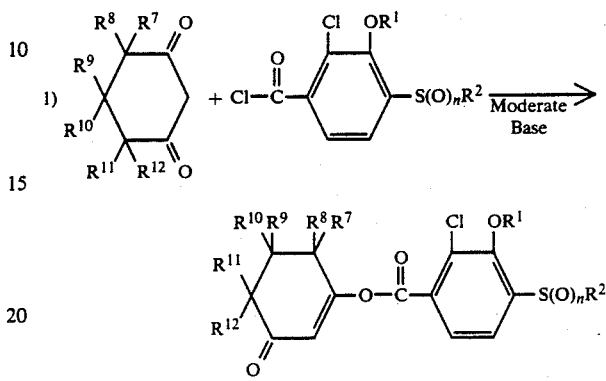

wherein n and $R^1$, $R^2$ and $R^7$ through $R^{12}$ are as defined above and the moderate base is such as tri-$C_1$-$C_6$ alkylamine, pyridine, alkali xetal carbonate or alkali metal phosphate.

Generally, in step (1) mole amounts of the dione and substituted benzoyl chloride are used, along with a slight mole excess of a moderate base. The two reactants are combined in an organic solvent such as acetonitrile, nethylene chloride, toluene, ethyl acetate or dimethylformamide. The base and benzoyl reactant preferably are added to the reaction mixture with cooling. The mixture is stirred at 0° C.-50° C. until the reaction is substantially complete The reaction product is worked up by conventional techniques.

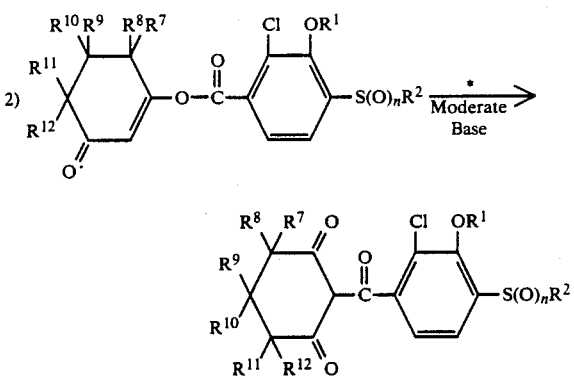

*cyanide source such as acetonecyanohydrin or KCN wherein $R^1$, $R^2$ and $R^7$ through $R^2$ are as defined above.

Generally, in step (2) a mole of the enol ester intermediate is reacted With 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or xethyl isobutyl ketone cyanohydrins; cyanchydrins of benzaldehyde or of $C_2$-$C_5$ aliphatic aldehydes such as acetaldehyde, propionaldihyde, etc., cyanohydrins; zinc cyanide; and hydrogen cyanide itself. Hydrogen cyanide is considered most advantageous as it produces relatively rapid reaction and is inexpensive. Among cyanohyrins the preferred cyanide source is acetone cyanohydrin.

The cyanide source is used in an amount up to about 50 mole % based on the enol ester. It may be used in as little as about 1 mole % to produce an acceptable rate of reaction at about 40° C. on a small scale. larger scale reactions give more reproducible results with slightly higher catalyst levels of about 2 mole %. Generally about 1–10 mole % of the cyanide source is preferred.

The process is conducted with a molar excess, with respect to the enol ester, of a moderate base. By the term "moderate base" is xeant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic base such as tertiary amines and inorganic bases such as alkali metal carbonate and phosphates. Suitable tertiary amines include trialkylamines such as triamethylamine, trialkanolamines such as triethanolamine, and pyridine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a transfer catalyst may be included in the reaction. Particularly suitable phase transfer catalysts are the Crown ethers.

A number of different solvents may be usable in this process, depending on the nature of the acid chloroform or the acylated product. A preferred solvent for this reaction is 1,2-dichloroethane. Other solvents which may be employed depending on the reactants or products include toluene, acetonitrile, xethylene chloride, ethyl acetate, dimethylformamide, and methel isobutyl ketone (MIBK).

In general, depending on the nature of the reactants and the cyanide source, the rearrangement may be conducted at temperatures up to about 50° C.

What is claimed is:

1. A compound having the structure formula

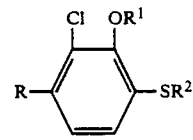

wherein R is carboxy, cyano or —$CO_2R_a$ wherein $R_a$ is $C_1$-$C_4$ alkyl; $R^1$ is $C_1$-$C_4$ alkyl, $C_1$-$C_4$ haloalkyl, —$CH_2CH_2OCH_3$, —$CH_2CH_2OC_2H_5$, —$CH_2CH_2SCH_3$ or —$CH_2CH_2SC_2H_5$ and $R^2$ is $C_1$-$C_4$ alkyl with the proviso that when R is carboxy, then $R^1$ is only —$CH_2CH_2OCH_3$, —$CH_2CH_2OC_2H_5$, —$CH_2CH_2SCH_3$ or —$CH_2CH_2SC_2H_5$.

2. The compound of claim 1 wherein R is carboethoxy; $R^1$ is $C_1$-$C_3$ alkyl, —$CH_2CH_2OCH_3$, —$CH_2CH_2OC_2H_5$ or —$CH_2CH_2$—$SC_3$; and $R^2$ is $C_1$-$C_4$ alkyl.

* * * * *